| United States Patent [19] | [11] Patent Number: 5,075,462 |
| Kuo et al. | [45] Date of Patent: Dec. 24, 1991 |

[54] PROCESS FOR THE PREPARATION OF QUINONES

[75] Inventors: Yeong-Jen Kuo; Michael Bellas, both of Kingsport, Tenn.

[73] Assignee: Eastman Kodak Company, Rochester, N.Y.

[21] Appl. No.: 593,132

[22] Filed: Oct. 5, 1990

[51] Int. Cl.$^5$ ............................................. C07C 46/06
[52] U.S. Cl. .................................. 552/299; 552/308; 552/309
[58] Field of Search ....................... 552/308, 309, 299

[56] References Cited

U.S. PATENT DOCUMENTS 3,796,732  3/1974  Brenner ............................. 552/309
4,482,493  11/1984  Matsumoto et al. ................ 552/309
4,632,782  12/1986  Komatsu et al. .................... 552/309

*Primary Examiner*—Jose G. Dees
*Attorney, Agent, or Firm*—J. Frederick Thomsen; William P. Heath, Jr.

[57] ABSTRACT

Disclosed is a process for the preparation of quinones by the catalytic oxidation of aromatic diols with a peroxide in the presence of a catalyst system comprising a cerium carboxylate and a cupric carboxylate.

5 Claims, No Drawings

PROCESS FOR THE PREPARATION OF QUINONES

This invention pertains to the preparation of quinones by the catalytic oxidation of aromatic diols. More specifically, this invention pertains to the preparation of quinones by the oxidation of aromatic diols with a peroxide in the presence of a catalyst system comprising a cerium carboxylate and a cupric carboxylate.

Quinones such as p-benzoquinone, methyl-p-benzoquinone, cyclohexyl-p-benzoquinone, phenyl-p-benzoquinone, o-benzoquinone, 1,4-naphthoquinone and the like are valuable chemical intermediates useful in the preparation of herbicides, dyes, photographic initiators and the like. p-Benzoquinone also is useful as an inhibitor in processing certain vinyl monomers such as acrylic acid and as a dehydrogenation agent.

Known processes for the manufacture of p-benzoquinone include the oxidation of aniline in the presence water, sulfuric acid and manganese dioxide. Most of the p-benzoquinone obtained from this process was converted to hydroquinone. U.S. Pat. No. 4,208,339 describes the preparation of p-benzoquinone by the oxidation of phenol with oxygen or an oxygen-containing gas in the presence of cuprous or cupric ions and a second metal such as nickel, iron, tin, cobalt, chromium, molybdenum or magnesium.

Most of the hydroquinone presently manufactured on a commercial scale does not produce p-benzoquinone as an intermediate. Therefore, the primary objective of the present invention is the preparation of quinones from the corresponding aromatic diols in general and the preparation of p-benzoquinone from hydroquinone (1,4-benzenediol) in particular.

H. Firouzabadi and N. Iranpoor, Synthetic Communications 14, 875 (1984) describe the preparation of benzoquinone compounds by the oxidation of a benzene solution of benzenediols such as hydroquinone and catechol using ceric trihydroxyhydroperoxide [Ce(OH)$_3$OOH] as the oxidizing agent. This non-catalytic process does not employ either air or a peroxide but uses two moles of the oxidizing agent per mole of the reactant. A. E Gekhman et al., Kinet. Katal. 30, 362 (1989) disclose the oxidation of hydroquinone to p-benzoquinone using oxygen or an oxygen-containing gas and salts of certain trivalent rare earth metals. The use of trivalent cerium, however, produced quinhydrone rather than p-benzoquinone.

There are many references in the literature to the use of copper compounds and copper complexes in the oxidation of phenolic compounds. The oxidation of hydroquinone with oxygen in the presence of a polyvinylpyridine-copper (II) complex and a poly(4-vinyl pyridine-co-N-vinylpyrrolidone)-copper (II) complex is described by K. Yamashita et al., Polymer Bulletin 22, 728 (1989) and in Makromol, Chem., Rapid Communication, 9 705 (1988). The use of copper (II)- and cobalt (II)-polyvinylpyridine complexes in the oxidation of 3,5-di-t-butylcatechol with oxygen is disclosed in the J. Mol. Catalysis 55, 379 (1989). The oxidation of hydroquinone using oxygen in the presence of copper (II)-polyelectrolyte complexes is disclosed in J. Pol. Sci. 15, 2059 (1977). R. J. Radel et al., Ind. Eng. Chem. Prod. Res. Dev. 21, 566 (1982) describe the oxidation of hydroquinone with oxygen at both atmospheric and under pressure using various Cu (I) and Cu (II) salts, Ru/C, Pd/C, V$_2$O$_5$, Ru/Al$_2$O$_3$, and Rh/Al$_2$O$_3$ as catalysts. T. R. Demmin et al., J. Am. Chem. Soc. 103, 5795 (1981) describe the catalytic conversion of catechols to o-benzoquinones using oxygen in the presence of copper (II) salts.

We have discovered that quinone compounds may be prepared in good yields by contacting an aromatic diol with a peroxide in the presence of an inert solvent and a catalyst system comprising a cerous (Ce$^{+++}$) carboxylate and a cupric carboxylate. Quinone compounds can be prepared by oxidizing an aromatic diol with a peroxide using a cerous carboxylate as the sole catalyst component. The use of other cerous salts has been found to give results substantially inferior to those which may be obtained in accordance with our invention. For example, ceric sulfate, cerous sulfate, cerium ammonium nitrate, cerium ammonium sulfate, cerous carbonate, and cerous nitrate have found to be much less effective than cerous acetate. While we do not wish to be bound by any particular theory regarding the operation of our process, it is believed that the cerous carboxylate salt is activated by the peroxide to form a cerium $^{+4}$ complex which oxidizes the diol reactant to the corresponding quinone.

The use of a cerous carboxylate in combination with a cupric carboxylate permits the use of a lower concentration of the more expensive cerous compound and also improves the filtration characteristics, e.g. filtration rates, of the reaction mixture. We have found that substantially inferior results are obtained when other metal salts such as cobalt acetate or manganese acetate are used as the cocatalyst instead of the cupric carboxylate compounds.

The aromatic diols which may be used in the process provided by the present invention include unsubstituted and substituted benzenediols, naphthalenediols, anthracenediols and the like. Examples of the substituents which may be presence on the substituted benzenediols and naphthalenediols include alkyl of up to about 12 carbon atoms, halogen such as chloro, cycloalkyl such as cyclohexyl and aryl such as phenyl. In addition to hydroquinone, specific examples of suitable aromatic diol reactants are 1,2-benzenediol, methyl-1,4-benzenediol, cyclohexyl-1,4-benzenediol, phenyl-1,4-benzenediol, 1,2- and 1,4-naphthalenediol, and the like. A preferred group of benzenediol reactants and quinone products have the general formulas

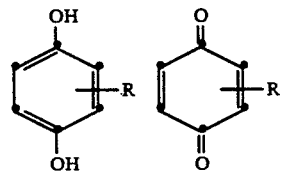

wherein R is hydrogen, alkyl of up to about 8 carbon atoms, halogen, cyclohexyl or phenyl.

Examples of the peroxides which may be used in our novel process include hydrogen peroxide; aliphatic peroxides such as alkyl peroxides, e.g., tertiarybutyl hydroperoxide; peracids such as percarboxylic acids i.e., a carboxylic acid peroxide, e.g., peracetic acid, perbutyric acid and perbenzoic acid; and the like. Hydrogen peroxide and peracetic acid are the preferred peroxides. The hydrogen peroxide suitable for use in the process comprises aqueous hydrogen peroxide having a peroxide content of 3 to about 90 weight percent. For economic and safety reasons, the aqueous hydrogen peroxide most suitable for use in the process has a hydrogen peroxide content of about 30 to 70 weight percent. It is well-known to those skilled in the art that peracetic acid may be generated in situ by several processes, the most important of which comprise the dissolution of hydrogen peroxide in acetic acid or acetic anhydride and the interaction of oxygen with acetaldehyde. These methods of in situ generation of the peroxide are within the scope of our invention. A particularly useful source of peracetic acid is the epoxidation process described by J.T. Lutz, Jr. in Kirk-Othmer, Encyclopedia of Chemical Technology, 3rd Ed., Vol. 9, p. 225-258 (1980). In the epoxidation process, peracetic acid is generated by contacting acetic acid with hydrogen peroxide in the presence of an acidic ion exchange resin.

The amount of peroxide employed in the process of the present invention can vary from 0.75 to 3.0 moles peroxide per mole of aromatic diol reactant. However, the best results are achieved by using about 0.95 to 1.1 moles peroxide per mole of diol reactant.

The cerous and cupric carboxylate catalyst components may be selected from cerous and cupric salts of various carboxylic, including dicarboxylic, acids such as cerous acetate, cupric acetate, cerous propionate, cupric propionate, cerous butyrate, cupric isobutyrate, cerous benzoate and the like. The combination of cerous and cupric carboxylates may be used in a mole ratio of cerous carboxylate:cupric carboxylate in the range of about 99:1 to about 10:90. However, to achieve the advantages provided by the present invention, the cerous carboxylate:cupric carboxylate mole ratio normally is within the range of about 80:20 to 40:60.

The catalytic amount of the cerium-copper catalyst system can be varied substantially depending, for example, on the reaction conditions and the particular catalyst system employed. Thus, the total moles of cerous carboxylate and cupric carboxylate employed may be used in amounts ranging from about 0.01 to 1 mole of catalyst components (total moles of cerous and cupric carboxylate) per mole of aromatic diol reactant. The preferred catalyst system wherein the cerous carboxylate:cupric carboxylate mole ratio is within the range of about 80:20 to 40:60 preferably is employed in an amount which gives a catalyst:diol reactant mole ratio of about 0.25:1 to 0.50:1. The catalyst system may be recovered and utilized in subsequent oxidations.

Our novel process is carried out in the presence of an inert solvent such as water, an aliphatic carboxylic acid such as acetic acid, mixtures of water and an aliphatic carboxylic acid and mixtures of an aliphatic carboxylic acid and a hydrocarbon such as benzene, toluene, hexane, heptane and the like. Normally, the amount of solvent employed gives a solvent:aromatic diol reactant weight ratio of about 5:1 to 20:1.

The process may be practiced at a temperature of about 0° to 80° C. although the use of temperatures in the upper portion of this range tends to cause some quinone degradation. The preferred temperature range is about 15° to 40° C. Reaction times of about 30 to 120 minutes normally give good results, e.g., quinone product yields of about 80 to 98% based on the aromatic diol reactant. The quinone product may be isolated according to conventional procedures such as by extraction, distillation, sublimation and the like.

The process of the present invention may be carried out in a batch, semi-continuous or continuous manner. In continuous operation of the process, a solution of the diol reactant, a catalyst solution comprising fresh catalyst and recycle catalyst solution, and a peroxide may be fed to a reaction zone comprising one or more reactors maintained at the appropriate reaction temperature. The effluent from the reaction zone containing the quinone product dispersed in the reaction mixture is fed to a product recovery zone wherein the reaction zone effluent is intimately mixed with a hydrocarbon such as toluene to obtain a hydrocarbon solution of the quinone product. After filtering to remove any insolubles present, the extraction mixture is fed to a separator wherein the hydrocarbon phase is separated from the remainder of the reactor mixture. The quinone product may be recovered from the hydrocarbon phase by crystallization which may include a concentration step in which a portion of the hydrocarbon solvent is removed by distillation. The remainder of the reaction mixture containing catalyst components and any unconverted diol reactant is removed from the product recovery zone recycled to the reaction zone.

A particularly preferred embodiment of the process provided by the present invention concerns the preparation of p-benzoquinone by contacting a solution of hydroquinone and a cerous carboxylate/cupric carboxylate catalyst system in an inert solvent with aqueous hydrogen peroxide or peracetic acid at a temperature of about 15° to 40° C.

The operation of our novel process is further illustrated by the following examples wherein GLC refers to gas/liquid chromatography.

EXAMPLE 1

A 1000 mL, 3-neck flask fitted with a thermometer and an addition funnel is charged with 200 mL of water, 8 g (0.025 mole) of cerous acetate, 5 g (0.025 mole) of cupric acetate, and 22 g (0.2 mole) of hydroquinone. The flask is immersed in a water bath to maintain the reaction mixture at a constant temperature. The solution is agitated with a mechanical stirrer at 25° C. for 5-10 minutes and then 22.2 mL of 30% aqueous hydrogen peroxide (0.22 mole $H_2O_2$) is slowly added to the solution over a period of about 1 hour. The temperature of the solution first increases to about 30°-35° C. and then decreases to 25° C. and remains at that temperature throughout the reaction. The total reaction time is 2 hours. At the completion of the reaction, 200 mL of toluene is added and a trace amount of solid formed during the reaction is removed by filtration. The organic phase is separated, the toluene is stripped off and the crude p-benzoquinone obtained is purified by sublimation. The yield of purified p-benzoquinone melting at 113.4° C. is 85%. The aqueous phase containing the catalyst components is recovered and saved for subsequent use.

EXAMPLE 2

Into a 50 mL, round-bottom flask equipped with a dropping funnel and a magnetic stirrer are placed 40 mL of water, 1.6 g (0.005 mole) of cerous acetate, 1 g (0.005 mole) of cupric acetate, and 4.4 g (0.04 mole) of hydroquinone. A total of 4.5 mL of 30% hydrogen peroxide is added dropwise to the reaction mixture with stirring. The reaction is continued at 25° C. for 2 hours. At the completion of the reaction, the mixture is poured into 40 mL of toluene and the toluene layer is separated. Assay of the toluene layer by GLC shows that the p-benzoquinone yield is 90%.

EXAMPLE 3

The procedure of Example 1 is repeated using 200 mL of water, 49.9 g of 30% aqueous hydrogen peroxide, 5 g (0.0144 mole) of cerous acetate, 5 g (0.025 mole) of cupric acetate, and 44 g (0.4 mole) of hydroquinone. The reaction is continued with stirring for 2 hours. At the completion of the reaction, the mixture is poured into 300 mL of toluene and the toluene layer is separated. Assay of the toluene layer by GLC shows that the p-benzoquinone yield is 80%.

EXAMPLE 4

The procedure of Example 2 is followed using 40 mL of water, 4.5 mL of 30% hydrogen peroxide, 1.92 g (0.006 mole) of cerous acetate, 0.8 g (0.004 mole) of cupric acetate, and 4.4 g (0.04 mole) of hydroquinone. The reaction is continued with stirring for 2 hours. At the completion of the reaction, the mixture is poured into 40 mL of toluene and the toluene layer is separated. Assay of the toluene layer by GLC shows that the p-benzoquinone yield is 90%.

EXAMPLE 5

The procedure of Example 2 is repeated using 40 mL of water, 4.5 mL of 30% aqueous hydrogen peroxide, 1.28 g (0.004 mole) of cerous acetate, 1.2 g (0.0066 mole) of cupric acetate, and 4.4 g (0.04 mole) of hydroquinone. The reaction is continued with stirring for 2 hours. At the completion of the reaction, the mixture is poured into 40 mL of toluene and the toluene layer is separated. Assay of the toluene layer by GLC shows that the p-benzoquinone yield is 74%.

COMPARATIVE EXAMPLE 1

The procedure of Example 2 is followed using 40 mL of water, 4.5 mL of 30% aqueous hydrogen peroxide, 1.6 g (0.005 mole) of cerous acetate, 1.25 g (0.005 mole) of cobalt acetate, and 4.4 g (0.04 mole) of hydroquinone. The reaction is continued with stirring for 2 hours. At the completion of the reaction, the mixture is poured into 40 mL of toluene and the toluene layer is separated. Assay of the toluene layer by GLC shows that the p-benzoquinone yield is 28%.

COMPARATIVE EXAMPLE 2

The procedure of Example 2 is repeated using 40 mL of water, 4.5 mL of 30% aqueous hydrogen peroxide, 1.6 g (0.005 mole) of cerous acetate, 1.23 g (0.0055 mole) of manganese acetate, and 4.4 g (0.04 mole) of hydroquinone. The reaction is continued with stirring for 2 hours. At the completion of the reaction, the mixture is poured into 40 mL of toluene and the toluene layer is separated. Assay of the toluene layer by GLC shows that the p-benzoquinone yield is 28%.

The invention has been described in detail with particular reference to preferred embodiments thereof, but it will be understood that variations and modifications may be effected within the spirit and scope of the invention.

We claim:

1. Process for the preparation of a quinone compound which comprises contacting an aromatic diol selected from the group consisting of benzenediols; benzenediols substituted with alkyl of up to about 12 carbon atoms, halogen, cyclohexyl and phenyl; naphthalenediols; and naphthalenediols substituted with alkyl of up to about 12 carbon atoms, halogen, cyclohexyl and phenyl; with a peroxide in the presence of an inert solvent and a catalyst system comprising a cerous carboxylate and a cupric carboxylate.

2. Process according to claim 1 wherein the aromatic diol is contacted with a peroxide selected from hydrogen peroxide and peracetic acid in the presence of an inert solvent and a catalyst system comprising a cerous carboxylate and a cupric carboxylate at a temperature of about 15° to 40° C. and wherein the mole ratio of the catalyst system:aromatic diol is about 0.25:1 to 0.50:1.

3. Process for the preparation of a quinone compound having the formula

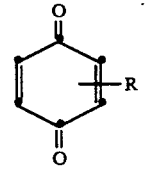

which comprises contacting an aromatic diol having the formula

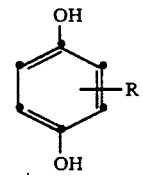

with a peroxide selected from hydrogen peroxide and peracetic acid in the presence of a catalyst system comprising a cerous carboxylate and a cupric carboxylate and an inert solvent at a temperature of about 15° to 40° C., wherein the mole ratio of the catalyst system to aromatic diol is about 0.25:1 to 0.50:1 and R is hydrogen, alkyl of up to about 8 carbon atoms, halogen, cyclohexyl or phenyl.

4. Process for the preparation of p-benzoquinone which comprises contacting a solution of hydroquinone and a catalyst system comprising a cerous carboxylate and a cupric carboxylate in an inert solvent with aqueous hydrogen peroxide or peracetic acid at a temperature of about 15° to 40° C.

5. Process according to claim 4 for the preparation of p-benzoquinone which comprises contacting a solution of hydroquinone and a catalyst system comprising cerous acetate and a cupric acetate in an inert solvent selected from water, acetic acid or a mixture thereof with aqueous hydrogen peroxide or peracetic acid at a temperature of about 15° to 40° C., wherein the mole ratio of the catalyst system to aromatic diol is about 0.25:1 to 0.50:1.

* * * * *